(12) United States Patent
Melgaard et al.

(10) Patent No.: US 11,160,487 B2
(45) Date of Patent: Nov. 2, 2021

(54) METHOD AND DEVICE FOR ANALYZING A CONDITION OF A HEART

(71) Applicant: AALBORG UNIVERSITET, Aalborg Øst (DK)

(72) Inventors: Jacob Melgaard, Svenstrup (DK); Johannes Jan Struijk, Terndrup (DK); Claus Graff, Klarup (DK)

(73) Assignee: AALBORG UNIVERSITET, Aalborg Øst (DK)

( * ) Notice: Subject to any disclaimer, the term of this patent is extended or adjusted under 35 U.S.C. 154(b) by 175 days.

(21) Appl. No.: 16/345,446

(22) PCT Filed: Nov. 3, 2017

(86) PCT No.: PCT/EP2017/078129
§ 371 (c)(1),
(2) Date: Apr. 26, 2019

(87) PCT Pub. No.: WO2018/083210
PCT Pub. Date: May 11, 2018

(65) Prior Publication Data
US 2019/0254552 A1 Aug. 22, 2019

(30) Foreign Application Priority Data
Nov. 4, 2016 (EP) .................................... 16197235

(51) Int. Cl.
*A61B 5/00* (2006.01)
*A61B 5/366* (2021.01)
(Continued)

(52) U.S. Cl.
CPC .............. *A61B 5/366* (2021.01); *A61B 5/316* (2021.01); *A61B 5/339* (2021.01); *A61B 5/7239* (2013.01);
(Continued)

(58) Field of Classification Search
CPC . A61B 5/0472; A61B 5/7239; A61B 5/04012; A61B 5/044; A61B 5/7278; A61N 1/3704; A61N 1/3627
See application file for complete search history.

(56) References Cited

U.S. PATENT DOCUMENTS 8,972,228 B2 3/2015 Ghosh et al.
9,078,573 B2 7/2015 Ramanathan et al.
(Continued)

FOREIGN PATENT DOCUMENTS

WO 2009/134170 A1 11/2009
WO 2015/090260 A2 6/2015
(Continued)

OTHER PUBLICATIONS

Del-Carpio Munoz, F., et al., "Delayed Intrinsicoid Deflection Onset in Surface ECG Lateral Leads Predicts Left Ventricular Reverse Remodeling After Cardiac Resynchronization Therapy," Heart Rhythm 10(7):979-987, Jul. 2013.
(Continued)

*Primary Examiner* — Scott M. Getzow
(74) *Attorney, Agent, or Firm* — Christensen O'Connor Johnson Kindness PLLC

(57) ABSTRACT

A method for analyzing a condition of a heart, comprises receiving a plurality of electric signals, which are acquired by non-invasive measurement on the skin of a person or animal, each signal representing electrical activity in a respective region of the heart of the person or animal; calculating a derivative value of each signal at a plurality of time instances; selecting a plurality of the calculated derivative values of a first signal and determining a first point in time of a first event based on the selected derivative values; selecting a plurality of the calculated derivative values of a second signal and determining a second point in time of a second event, corresponding to the first event, based on the
(Continued)

selected derivative values of the second signal, and calculating at least one measure based on a difference of the first point in time and the second point in time.

20 Claims, 7 Drawing Sheets

(51) Int. Cl.
    *A61N 1/37*          (2006.01)
    *A61N 1/362*        (2006.01)
    *A61B 5/316*        (2021.01)
    *A61B 5/339*        (2021.01)

(52) U.S. Cl.
    CPC .......... *A61B 5/7278* (2013.01); *A61N 1/3627* (2013.01); *A61N 1/3704* (2013.01)

(56) References Cited

U.S. PATENT DOCUMENTS

| 9,510,763 | B2 | 12/2016 | Ghosh et al. |
| 2010/0191134 | A1 | 7/2010 | Frank et al. |
| 2012/0283587 | A1 | 11/2012 | Gosh et al. |
| 2012/0284003 | A1 | 11/2012 | Gosh et al. |
| 2013/0131529 | A1 | 5/2013 | Jia et al. |
| 2014/0371807 | A1* | 12/2014 | Ghosh .................. A61N 1/3627 607/28 |
| 2015/0216434 | A1 | 8/2015 | Ghosh et al. |
| 2016/0256063 | A1* | 9/2016 | Friedman ............... A61B 5/686 |

FOREIGN PATENT DOCUMENTS

| WO | 2015/150831 A1 | 10/2015 |
| WO | 2015/175469 A1 | 11/2015 |

OTHER PUBLICATIONS

International Search Report and Written Opinion dated Jan. 2, 2018, issued in corresponding International Application No. PCT/EP2017/078129, filed Nov. 3, 2017, 11 pages.

Jurak, P., et al., "Ultra-High-Frequency ECG Measurement," Computing in Cardiology 40:783-786, 2013.

Strauss, D.G., et al., "Defining Left Bundle Branch Block in the Era of Cardiac Resynchronization Therapy," American Journal of Cardiology 107(6):927-934, Mar. 2011.

* cited by examiner

METHOD AND DEVICE FOR ANALYZING A CONDITION OF A HEART

TECHNICAL FIELD

The present invention relates to a method and device for analyzing a condition of a heart of a person or animal.

BACKGROUND

The normal functioning heart is controlled by electrical signals that prompt the muscle of the heart to contract. Correct propagation of the signals is crucial in order for the heart to maintain a healthy heartbeat. The electromechanical process is initiated at the sinoatrial node (SA node) of the heart, which acts as a natural pacemaker, regulating the regular and rhythmic pattern of the heartbeat. The electrical wavefront spreads from the SA node throughout the two upper chambers of the heart, the atria, causing the muscles of the upper chambers to contract. The depolarization signal further activates the atrioventricular node (AV node), which after a delay, relays the signal to ventricular chambers of the heart, causing the ventricles to contract. This mechanical contraction of the atria and ventricles drives the blood flow in the human body and it is vital that the coordination of the different parts of the heartbeat is provided in a timely manner and with great precision.

When a conducting branch that handles normal electrical activation is blocked or in any other way obstructed, a dyssynchronous ventricular contraction may arise, leading to low pumping efficiency and heart failure.

U.S. Pat. No. 8,972,228 teaches techniques for evaluating cardiac electrical dyssynchrony. In some examples, an activation time is determined for each of a plurality of torso-surface potential signals. The dispersion or sequence of these activation times may be analyzed or presented to provide a variety of indications of the electrical dyssynchrony of the heart of the patient. In some examples, the locations of the electrodes of the set of electrodes, and thus the locations at which the torso-surface potential signals were sensed, may be projected on the surface of a model torso that includes a model heart. The inverse problem of electrocardiography may be solved to determine electrical activation times for regions of the model heart based on the torso-surface potential signals sensed from the patient. However, the document leaves room for improvement.

Cardiac resynchronization therapy (CRT) by implantation of a pacemaker is used to resynchronize the electromechanical contractions of the compartments of a heart. The procedure may help the patient live a healthier life and reduces heart failure. However, there is a substantial portion (40-50%) of non-responders that are treated with CRT, to little effect.

A more effective method to visualize and quantify dyssynchrony in patients is therefore needed.

SUMMARY

In view of the above, it is an object of the present invention to provide a method enabling visualization and quantification of cardiac dyssynchrony. It is another object to visualize and quantify dyssynchrony such that an analysis may be made for the purpose of, for example, selecting patients for cardiac resynchronization therapy (CRT), guiding location of pacemaker leads for CRT and adjusting stimuli settings for CRT.

According to a first aspect, a method for analyzing a condition of a heart of a person or animal is provided. The method comprises receiving a plurality of electrical signals, which are acquired by non-invasive measurement on the skin of a person or animal, each signal representing electrical activity in a respective region of the heart of the person or animal, wherein the electrical activity contributes to controlling mechanical activation of the heart, calculating a derivative value of each signal at a plurality of time instances, wherein the plurality of time instances is within a time domain of a heartbeat of the heart, selecting a plurality of the calculated derivative values of a first signal among the plurality of signals and determining a first point in time of a first event based on the selected derivative values of the first signal, selecting a plurality of the calculated derivative values of a second signal among the plurality of signals and determining a second point in time of a second event, corresponding to the first event, based on the selected derivative values of the second signal, and calculating at least one measure based on a difference of the first point in time and the second point in time.

The step of determining a first point in time of a first event based on the selected derivative values of the first signal may comprise determining at least a first point in time of a first event based on the selected derivative values of the first signal. Likewise, the step of determining the second point in time of a second event, corresponding to the first event, based on the selected derivative values of the second signal, may comprise determining at least a second point in time of a second event, corresponding to the first event, based on the selected derivative values of the second signal. Consequently, the step of calculating at least one measure based on a difference of the first point in time and the second point in time may comprise calculating at least one measure based on a difference of the at least first point in time and the at least second point in time.

By calculating a measure based on a difference between a first and a second point in time, a condition of the heart may be quantified by means of an operation which may be quickly performed and requires a low amount of signal processing. The measure may be used to efficiently determine findings of intermediate diagnostic relevance, which may be utilized to determine e.g. whether the heart suffers from dyssynchrony and if proper adjustment by using, for example a pacemaker, is needed.

The method is based on calculating derivative values of electrical signals obtained at the skin of a person or animal, which implies that there is no need to transform acquired signals to a representation of the actual signal propagation in the heart (such as by solving the inverse problem of electrocardiography).

The method is further based on an insight that a difference between a first point in time of a first event in a first signal and a second point in time of a second event in a second signal may be used to analyze a heart condition. Thus, instead of analyzing the respective signals that represent the electrical activity in respective regions, points in time in the signals may be compared to each other. This provides a simple and powerful measurement for identifying e.g. dyssynchrony.

The method enables an analysis to be performed on a single heartbeat, which facilitates real-time analysis of a condition of the heart of a person or animal. This may be particularly useful e.g. if the method is performed to aid implantation of a pacemaker for guiding placement of leads of the pacemaker or to aid in setting pacemaker stimuli.

Thus, by enabling a method to identify dyssynchrony, three challenges to successful cardiac resynchronization therapy (CRT) may, among others, be relieved:

Selecting patients with cardiac dyssynchrony who will benefit from resynchronization of their ventricles by implantation of a biventricular pacemaker;

Guide placement of pacemaker leads during pacemaker implantation to achieve optimal synchrony between left and right ventricles;

Optimize settings of pacemaker stimuli and delays between stimuli, such as atrioventricular (AV) delay or interventricular (VV) delay, to increase benefit from resynchronization therapy in patients with biventricular pacemakers.

In addition to the measure determined by means of the method of the first aspect, other measures which may be helpful in analyzing a condition of the heart may be determined.

Drugs, sodium channel blockers in particular, but also other classes of drugs, may alter the contractility, or contractile force, of the heart muscle. It could be a possible application to use the disclosed method to quantify the effect of such drugs.

Several patients who receive ordinary cardiac pacemakers regress, shortly after implantation, to a state of heart failure where they need cardiac resynchronization therapy (CRT) with a biventricular pacemaker. Another possible application could be to use the method to identify those patients to improve their treatment.

Grading severity, grade and acuteness of ischemia (and the following infarction) is a subject where current methods are inadequate and inaccurate. Since the lack of oxygen to the tissue change the conduction speed through the tissue, yet another possible application of the disclosed method could be to quantify grade, severity and acuteness of ischemia, and whether the ischemic region is subendocardial or transmural.

In an embodiment, a method for analyzing a condition of a heart of a person or animal is provided. The method comprises receiving a plurality of electrical signals, which are acquired by non-invasive measurement on the skin of a person or animal, calculating a derivative value of a first signal at at least one time instance and determining a first point in time of a first event based on the calculated derivative value of the first signal, calculating a derivative value of a second signal at at least one time instance and determining a second point in time of a second event, corresponding to the first event, based on the calculated derivative value of the second signal, and calculating at least one measure based on a difference of the first point in time and the second point in time.

The signals are preferably acquired by electrocardiography using electrodes placed on the skin of a person or animal. The acquired signals stem from the depolarization or repolarization of the heart cells, giving rise to electrical waves propagating throughout the heart. In the text, the term "amplitude" will be used as a representation of a signal strength of the signal acquired on the skin of the person or animal.

In the context of this application, "dyssynchrony" should be construed as any undesired or abnormal delay of electrical activity between different regions of the heart. The dyssynchrony may for instance be between the atria and the ventricles or between a left and a right side of the heart, or between the base and the apex of the heart, or between the septum and free wall of the heart. Thus, a state of dyssynchrony is a state that is different from the electrical propagation of a healthy heart, even though the electrical signals of a healthy heart are not exactly simultaneous in all regions of the heart.

An electrical signal acquired on a specific position on the skin of a person or animal may correspond to electrical activity in a specific region of the heart. By means of acquiring electrical signals in different positions on the skin of the person or animal, signals representing electrical activity in different regions of the heart may be acquired. Hence, each signal may represent electrical activity of a region of the heart, without it being necessary to calculate the actual electrical activity corresponding to the acquired signal on the skin of the person or animal. It should also be realized that the acquired signals may represent electrical activity in overlapping regions, and by measuring electrical activity from different angles, a representation of electrical activity in a region (even a large portion of the heart) may be acquired so as to allow conclusions to be drawn on electrical propagation in the heart.

The time instances are specified points in time at which signals are acquired. The time instances may be within the time domain of a heartbeat, wherein a heartbeat is considered an activity arising from the heart electrical and/or mechanical activity. The time domain of a heartbeat should thus be construed as the time between, and including, the onset of electrical activation of the atria to, and including, the relaxation of the ventricles. In the context of this application, the term "time domain of a heartbeat" should also be construed as a time domain of signals in the heart arranged to trigger a heartbeat, even if the heart does not actually perform the mechanical contraction of the atria and/or ventricles (e.g. due to heart failure).

The "derivative value" may be a value calculated as a slope at a point of a continuous curve. However, in the context of this application, the term "derivative value" may also be construed as the value of the difference of the amplitude of a signal between two points, such as the difference between two values of electrical activity at different time instances, as calculating a difference is a common manner of determining a derivative value in digital domain. It may for example, in the case of identical lengths of time instances, be preferable to use differences as derivative values. Further, a signal may be represented as a sequence of discrete values at corresponding time instances. Thus, a derivative value of each signal at a specific time instance may be determined as the value of a difference between the amplitude at the given specific time instance and the amplitude at a previous time instance in the sequence.

The calculated derivative values may be used in order to determine an event. In the context of this application, the term "event" should be construed as any identification that may be analytically made in the signal. The event may thus have a corresponding physiological explanation, such as an onset of a QRS complex, but the event need not have a specific corresponding physiological explanation. For instance, the event may be a maximum negative derivative value of the signal.

Further, the definition that a second event corresponds to a first event should be construed as the events in the respective first and second signals being determined in the same manner, such as representing the onset of the QRS complex in the respective signals or the maximum negative derivative values in the respective signals. The definition may also be construed as the events in the respective first and second signals being determined in a predefined manner, such as representing the maximum negative derivative values in the respective signals, or the beginning and end in the respective signals.

The measure calculated based on the difference of the first point in time and the second point in time may be a direct measure of a time duration between the first point in time and the second point in time. This is advantageous compared to measuring activation times between two points in each of the plurality of electrical signals, because it is a direct way of quantifying dyssynchrony that does not require interval measurements to be performed in each of the plurality of electrical signals. However, the measure may also or alternatively be a percentage of the time duration in relation to a set value representing dyssynchrony, or even a more advanced analysis of the first and second points in time.

It should also be realized that more than two signals may be analyzed to determine further points in time for events in the respective signals. The measure may thus be based on several points in time, including the first and second points in time.

Further, several groups of signals may be defined, e.g. representing the left and right sides or the heart, respectively. Then, the first point in time may be used within a first group of signals to determine a representative point in time for the first group of signals. Similarly, the second point in time may be used within a second group of signals to determine a representative point in time for the second group of signals. Thus, the calculated measure may be determined based on these representative points in time for the first and the second signals, which should also be construed as being based on a difference of the first point in time and the second point in time.

It should also be understood that several measures may be calculated based on the received signals. Thus, in addition to calculating at least one measure based on the difference of the first point in time and the second point in time, other measures may also be calculated and used in analysis of a condition of the heart. For instance, a duration of negative derivative values within the signals may be used as measures of electrical propagation in the respective region of the heart.

It should be understood that the calculating of derivative values and selecting of a plurality of derivative values may be performed in different manners, e.g. by first deciding on a time range and then calculating derivative values within the time range and selecting all calculated derivative values. According to one alternative, derivative values may continuously be calculated for a signal and then calculated derivative values may be selected in a time range of interest. It should also be realized that other combinations of calculating derivative values within a time range and selecting some of the calculated derivative values may be used.

It should also be understood that a large number of electrical signals may be received. Thus, the plurality of electrical signals may be received and derivative values may be calculated for each of these signals. However, even further electrical signals may be received, which then would not be part of the plurality of electrical signals, for which derivative values are calculated and selected in order to calculate a measure.

In an embodiment, the plurality of time instances is within a QRS complex. By means of choosing a QRS complex, an entire heartbeat need not be analyzed. Further, a dyssynchrony may be determined based only on the QRS complex.

In a further embodiment, the plurality of time instances is within a single QRS complex. This implies that a condition of the heart may be determined for single heartbeats, allowing a measure to be quickly determined and also allowing a measure to be updated for each heartbeat. This may be especially advantageous in aiding implantation of a pacemaker, as a direct feedback may be given during placement of leads of the pacemaker and adjustment of stimuli settings.

In a further embodiment, the plurality of time instances is within a P-wave, a T-wave, or a ST-segment. By means of choosing a P-wave, a T-wave, or a ST-segment, an entire heartbeat need not be analyzed. Further, a dyssynchrony may be determined based only on the P-wave, a T-wave, or a ST-segment.

In a further embodiment, the plurality of time instances is within a single P-wave, T-wave, or ST-segment. The advantages described above in relation to the QRS complex also applies to this embodiment.

It should be realized that it is not necessary to use time instances only from a single QRS complex. On the contrary, an electrical signal may e.g. be averaged over a number of heartbeats or the signal from a number of heartbeats may be otherwise combined to form a representation of a signal within a QRS complex for which derivative values may be calculated.

In yet another embodiment, the derivative value is a first derivative value. This is a simple manner of determining a variation in a signal. However, it should be realized that a second or higher order derivative may be determined instead.

In an embodiment, the selected derivative values of the first signal and the selected derivative values of the second signal have been calculated at the same time instances in a range of time instances from onset of a QRS complex in the first signal to offset of the QRS complex in the second signal.

This implies that the derivative values of the first and second signals are calculated in a common time interval. Thus, for each time instance, there is determined a derivative value of both the first signal and the second signal. The onset of the QRS complex in the first signal may occur before onset of the QRS complex in the second signal. Likewise, the offset of the QRS complex in the second signal may occur after offset of the QRS complex in the first signal. Thus, derivative values of both the first and the second signals may be determined outside the QRS complex in the respective signals. By determining the derivative values for a common time interval, comparison of the signals is facilitated.

In an embodiment, the selected derivative values of the first signal and the selected derivative values of the second signal have been calculated at the same time instances in a range of time instances from onset of a P-wave, T-wave, or ST-segment in the first signal to offset of the P-wave, T-wave, or ST-segment in the second signal. The advantages described above in relation to the QRS-complex also applies to this embodiment.

In an embodiment, the time instances of the selected derivative values of the first and second signal are from the same stage of the QRS complex. This implies that the derivative values of the first and second signals need not be determined in a common time interval. Rather, the derivative values for the respective signals may only be determined for specific stages of the QRS complex, such as the entire QRS complex, within the signal. Hence, the derivative values may only be calculated for relevant time instances in the respective signals.

In an embodiment, the time instances of the selected derivative values of the first and second signal are from the same stage of the P-wave, T-wave, or ST-segment. The advantages described above in relation to the QRS-complex also applies to this embodiment.

In yet another embodiment, the calculating of at least one measure further comprises comparing a mean value of the selected derivative values of the first signal to a mean value of the selected derivative values of the second signal. This implies that the calculated at least one measure may comprise not only a measure based on the differences in points of time but also further measures based on differences in derivative values.

In yet another embodiment, the calculating of at least one measure further comprises comparing a maximum value of the selected derivative values of the first signal to a maximum value of the selected derivative values of the second signal.

In yet another embodiment, the calculating of at least one measure further comprises comparing a minimum value of the selected derivative values of the first signal to a minimum value of the selected derivative values of the second signal.

In yet another embodiment, the calculating of at least one measure further comprises comparing a number of the selected derivative values of the first signal to a number of the selected derivative values of the second signal.

In a further embodiment, the calculated measure is representative of a time shift between occurrence of a negative or positive slope of a QRS complex in the first signal and occurrence of a negative or positive slope of a QRS complex in the second signal. The negative slope of a QRS complex may be easily identified in the respective signal, which allows the time shift to be easily determined as a measure of dyssynchrony.

According to a second aspect, a method for analyzing a condition of a heart of a person or animal is provided. The method comprises receiving a plurality of electrical signals, which are acquired by non-invasive measurement on the skin of a person or animal, each signal representing electrical activity in a respective region of the heart of the person or animal, wherein the electrical activity contributes to controlling mechanical activation of the heart, calculating a derivative value of each signal at a plurality of time instances, wherein the plurality of time instances is within a time domain of a heartbeat of the heart extending at least from onset of a QRS complex in a first signal to offset of the QRS complex in a second signal, selecting a plurality of the calculated derivative values of the first signal among the plurality of signals, selecting a plurality of the calculated derivative values of the second signal among the plurality of signals, and comparing each of the selected derivative values of the first signal and each of the selected derivative values of the second signal to at least one threshold value.

The above mentioned features of the method according to the first aspect, when applicable, apply to this second aspect as well. In order to avoid undue repetition, reference is made to the above.

According to the method of the second aspect, information from the acquired electrical signals is extracted in a manner such that visualization of a condition of a heart is facilitated. Derivative values are calculated for a common interval of a first and a second signal spanning the entire QRS complex in the first signal and the entire QRS complex in the second signal, the QRS complex occurring before or simultaneously with the QRS complex of the second signal.

Thanks to the comparison of each selected derivative value to at least one threshold value, the selected derivative values may be represented by the relation to the at least one threshold value.

Thanks to the method according to the second aspect, the selected derivative values from common time intervals for both the first and the second signals may thus be represented simply in relation to at least one common threshold value. This may allow e.g. for powerful visualization of how the first and second signals develop by arranging a representation of the derivative values in relation to the at least one threshold value of the first and second signals on a common time axis.

In an embodiment, the selected derivative values are assigned a first state if the selected derivative value is positive and a second state if the selected derivative value is negative. This implies that positive and negative derivative values are distinguished. It may be sufficient to differentiate between positive and negative derivative values in order to be able to visualize acquired electrical signals in order to allow recognition of a dyssynchrony in the heart. The assigning of derivative values to the first and second states may be very quickly performed requiring small processing resources while allowing visualization of acquired signals in real-time.

The first and second state may each be associated with a respective color allowing derivatives of the signals to be presented using two colors illustrating whether the derivative of the signal is positive or negative. The first and second states may alternatively be associated with other features allowing presentation of the derivatives of the signals, such as "+" for a positive derivative value and "−" for a negative derivative values, or arrows pointing up and down, respectively.

In a further embodiment, the selected derivative values are compared to a color scale for assigning a color to each selected derivative value. This implies that a color of the derivative of a signal may be assigned to each time instance depending on the derivative value.

In yet another embodiment, the method further comprises outputting color information based on the assigned colors to a display for presenting a color-coding of the selected derivative values on the display. This implies that a color map of the derivatives of signals may be presented on the display, which allows an operator to quickly get an overview of how the first and second signals develop in the form of a color map and the operator may thus quickly draw conclusions based on the color map, even on dyssynchrony occurring in single heartbeats.

According to a third aspect, a computer program product is provided. The computer program comprises a computer-readable medium with computer-readable instructions such that when executed on a processing unit the computer program will cause the processing unit to perform a method according to any one of the embodiments of the first or the second aspect.

The above mentioned features of the methods according to the first and second aspects, when applicable, apply to this third aspect as well. In order to avoid undue repetition, reference is made to the above.

According to a fourth aspect, a device for analyzing a condition of a heart of a person or animal is provided. The device comprises a processing unit, wherein the processing unit is configured to: receive a plurality of electrical signals, which are acquired by non-invasive measurement on the skin of a person or animal, each signal representing electrical activity in a respective region of the heart of the person or animal, wherein the electrical activity contributes to controlling mechanical activation of the heart, calculate a derivative value of each signal at a plurality of time instances, wherein the plurality of time instances is within a time domain of a heartbeat of the heart, select a plurality of the calculated derivative values of a first signal among the plurality of signals, select a plurality of the calculated derivative values of a second signal among the plurality of signals, and calculate a measure based on the selected derivative values of the first signal and the selected derivative values of the second signal.

The above mentioned features of the method according to the first aspect, when applicable, apply to this fourth aspect as well. In order to avoid undue repetition, reference is made to the above.

The device may be used as a tool in analyzing a condition of a heart, e.g. for identifying of dyssynchrony. The device may provide a tool which is very simple to use and provides an analysis of measurements such that an operator may be able to easily assess a condition of a heart.

In an embodiment, the device comprises electrocardiogram leads for acquiring said plurality of electrical signals. The device may thus provide a complete system for acquiring electrical signals and analyzing the acquired electrical signals to allow quantification of a condition of the heart.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles "a," "an," "the," and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

BRIEF DESCRIPTION OF THE DRAWINGS

The above and other aspects of the present invention will now be described in more detail, with reference to appended drawings showing embodiments of the invention. The figures should not be considered limiting the invention to the specific embodiment; instead they are used for explaining and understanding the invention.

As illustrated in the figures, the sizes of layers and regions may be exaggerated for illustrative purposes and, thus, are provided to illustrate the general structures of embodiments of the present invention. Like reference numerals refer to like elements throughout.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and to fully convey the scope of the invention to the skilled person.

The heart is an electrically activated mechanical pump. Electrical activation of cardiac muscle cells leads to contraction. When one cell is electrically activated, the cell will activate neighboring cells, causing electrical activation wavefronts to propagate.

The sum of all wavefronts makes up the amplitude of an electrocardiogram. To acquire the signals produced by the wavefronts, electrodes are placed at specific positions on the torso and possibly other parts of the body, such as on the limbs, each position providing a sensory view of the heart from different angles.

Figure 1:
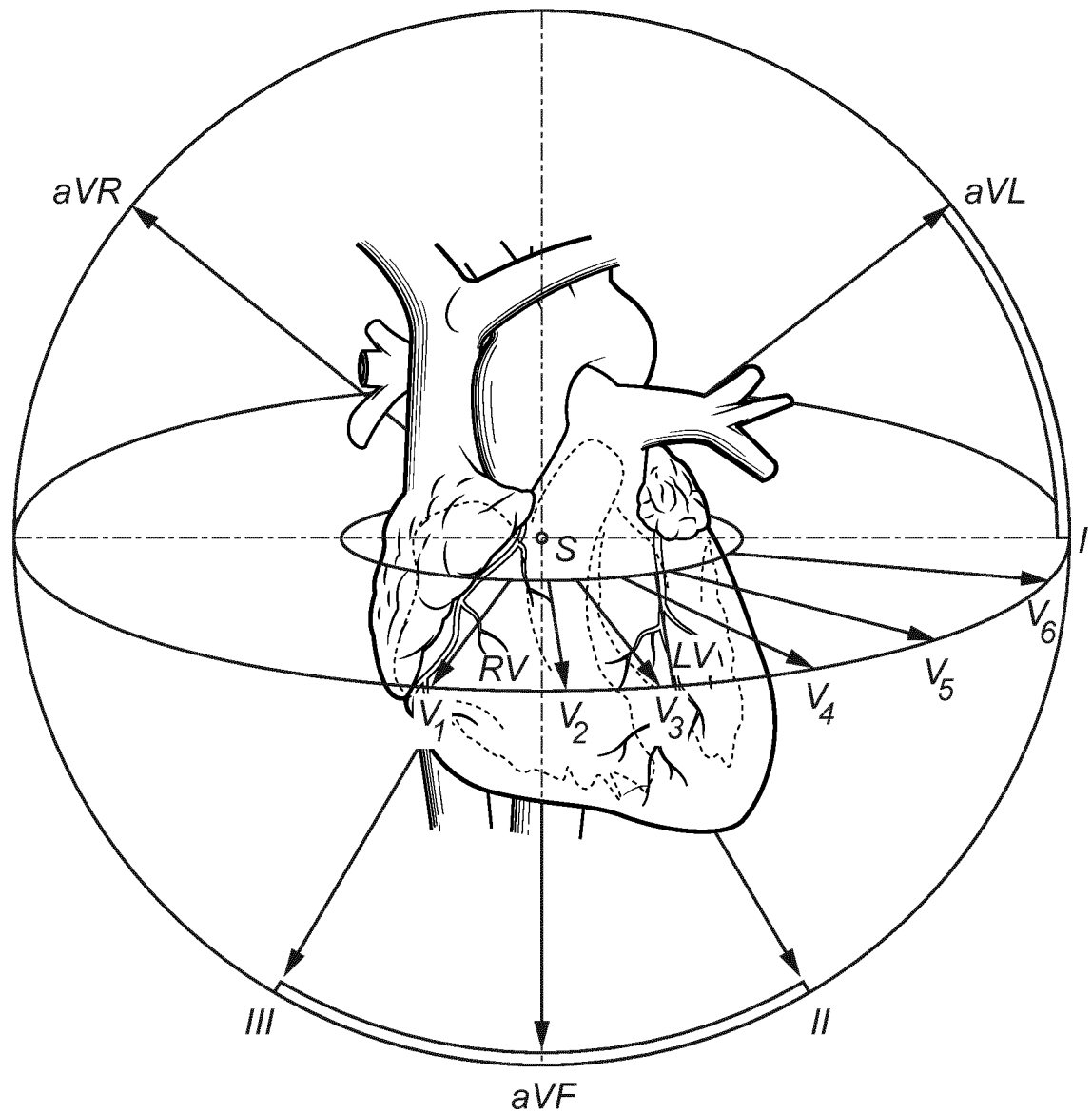
FIG. 1 illustrates a model of a heart and the different directions in which electrical signals from the heart may be acquired by the 12 leads of a standard electrocardiogram (ECG).

Now referring to FIG. 1, a model of a heart including angular directions of 12 leads used in acquiring of a standard electrocardiogram (ECG), is illustrated. Leads V1 to V6 provide signals corresponding to the horizontal activation of the heart muscles. Leads V1 to V6 can therefore provide information about the activation coordination in a horizontal plane of the heart.

Correspondingly, leads III to aVL (the full sequence may be observed in FIG. 2), show the sequential and vertical activation of the heart muscles. Leads III to aVL can therefore provide information about the activation coordination in a frontal plane of the heart.

A lead is configured to be arranged on the skin of the person or animal, viewing the heart from a respective angle. The lead may thus be arranged to acquire an electrical signal, which represents electrical activity in a corresponding region of the heart.

Figure 2:
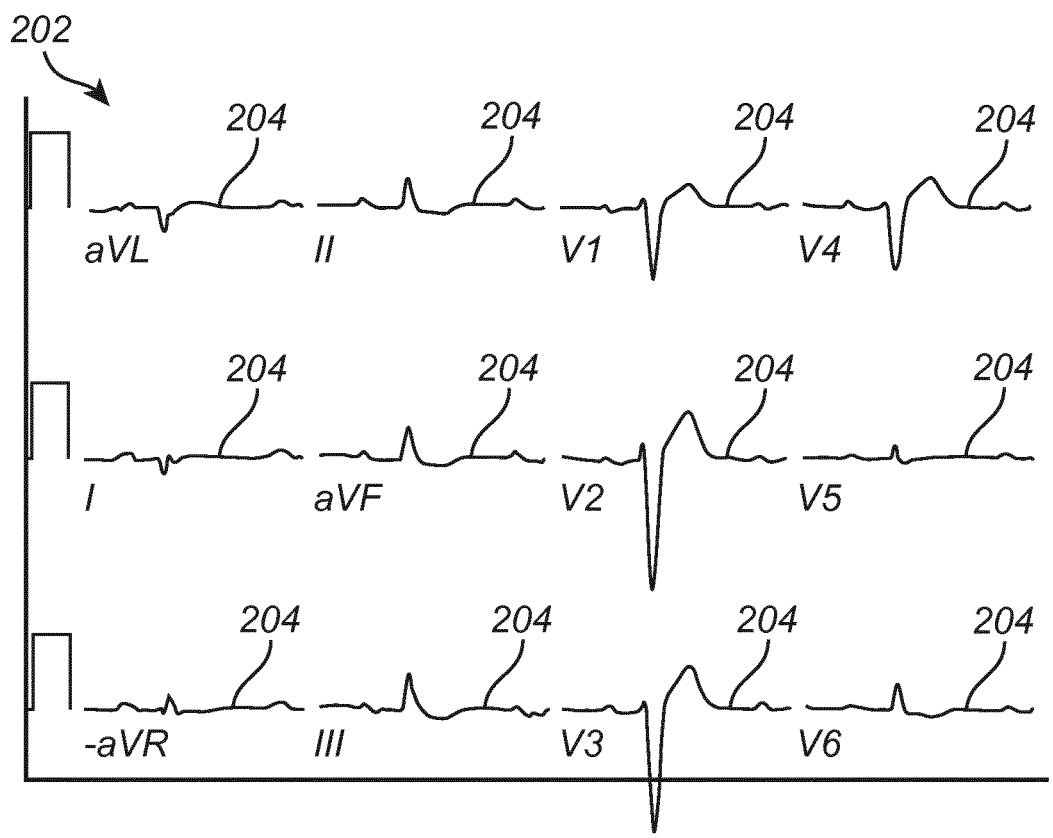
FIG. 2 illustrates a standard 12-lead electrocardiogram.

An electrocardiogram is shown in FIG. 2, displaying signals from the 12 leads described above with reference to FIG. 1. FIG. 2 thus illustrates a plurality of electrical signals 202 which may be acquired by the respective leads.

The ECG of a single heartbeat includes a P wave representing atrial depolarization, a QRS complex representing ventricular depolarization, a ST-segment representing the isoelectric period when the ventricles are in between depolarization and repolarization, and a T wave representing ventricular repolarization. Each lead may acquire an electrical signal representing one or more heartbeats including the different parts of the ECG, and analysis of the signals may allow visualization and quantification of a condition of the heart.

The present disclosure is made with examples referring to the QRS complex of the ECG. However, it is to be understood that the same technique can be applied to e.g. the P-wave, T-wave, or ST-segment, while achieving similar effects and advantages.

Figure 3:
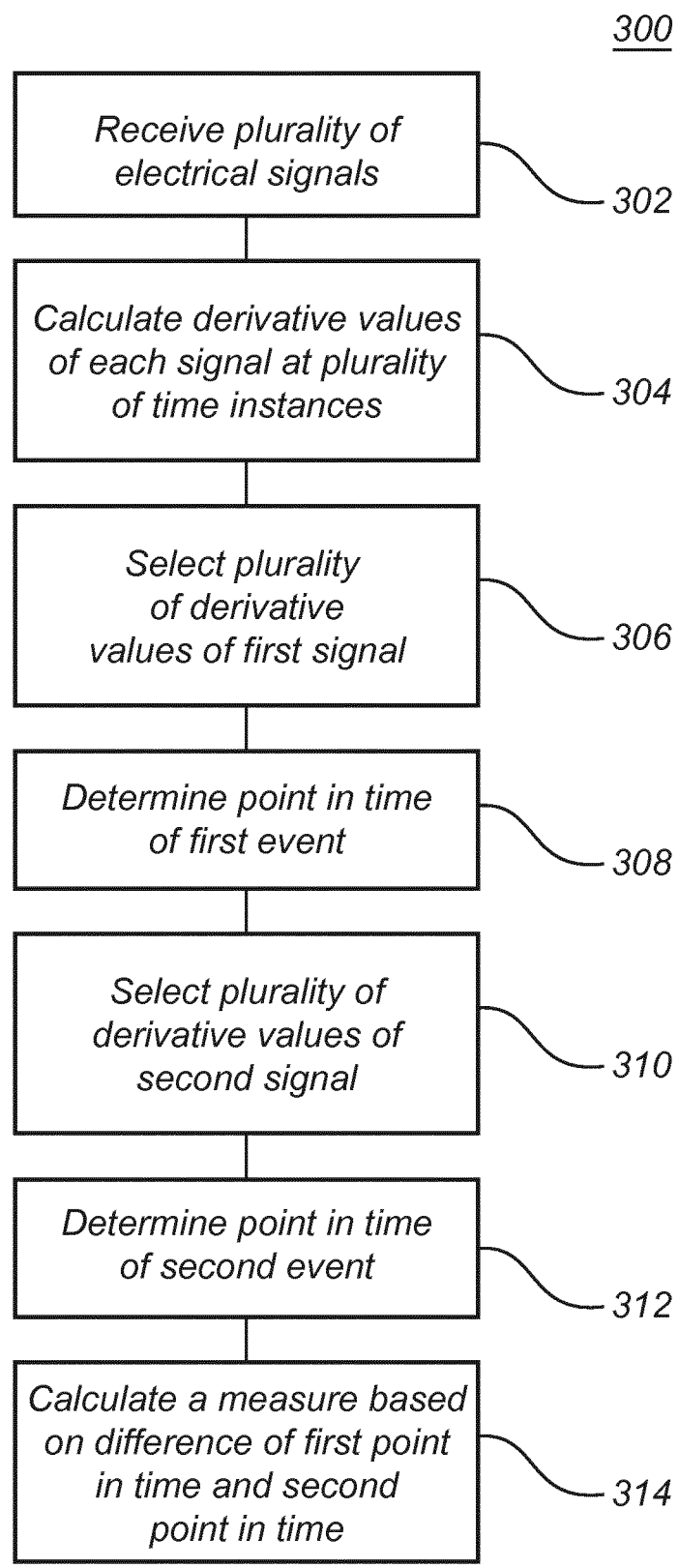
FIG. 3 shows a flowchart of a method according to an embodiment.

Now referring to FIG. 3, a method 300 according to an embodiment of the invention is described. The condition of a person's or animal's heart may be analyzed using the method 300.

According to an embodiment of the invention a plurality of electrical signals 202 is received, step 302. The plurality of signals 202 may constitute the signals acquired by leads used in acquiring of a standard ECG. In particular, the plurality of signals 202 may form the signals acquired by the 12 leads used in acquiring of a standard ECG, the leads being, V1-6, aVL, I, –aVR, II, aVF and III.

The plurality of signals 202 may originate at different regions of the heart of the person or animal. A signal 204 among the plurality of signals may thus represent electrical activity in a respective region of the heart. Even though each signal 204 represents electrical activity from a specific region of the heart, electrical activity may be represented by several signals among the plurality of signals 202.

The electrical activity contributes to controlling mechanical activation of the heart. As the electrical wavefronts spread throughout the heart, from the atria to the ventricles, the compartments of the heart contract driving the blood flow of the person or animal.

The received electrical signals may be analyzed. The analysis may be performed in a digital domain, such that a digital representation of the electrical signals is received or, that the received electrical signals are passed through an analog-to-digital converter.

A numerical amplitude of the electrical activity may be measured and stored for each of the signals 204 of the plurality of signals 202, at different time instances. The amplitudes may be stored one by one in association with different time instances. The amplitudes may be stored during acquiring of an ECG. The amplitudes may also or alternatively be stored after the ECG is partly or completely acquired.

An electrical signal 204 may thus be represented as a sequence of amplitude values associated with respective time instances. This sequence may e.g. be represented as an array of data values.

The time instances may be predetermined and set before the ECG has started, e.g. with a predetermined period between sequential time instances. The temporal location and interval between time instances may also be controlled during acquiring of the ECG. Thus, during one or more heartbeats, amplitude values of the electrical signals 204 may continuously be acquired and associated with respective time instances, or time stamps.

A derivative value may be calculated, step 304, of each signal 204 at a plurality of time instances. The derivative value may be calculated by determining the slope of a given signal 204. The derivative value may also be calculated by determining the difference between two sequential amplitudes, for example by comparing the amplitude at a given time instance and comparing it to the amplitude at the previous time instance.

The signal 404 may be smoothed or processed in other ways before the calculation of derivative values.

The derivative values may be stored in association with their respective time instances, e.g. as a sequence of derivative values with respective time instances.

The derivative values for two or more of the signals 204 may be further analyzed. Below, reference will be made to a first signal and a second signal. However, it should be realized that all of the signals 204 in the plurality of signals 202 may be used. Also, a group of at least two signals may be used, such as the signals of leads V1-V6 or the signals of leads III-aVL.

Figure 4A:
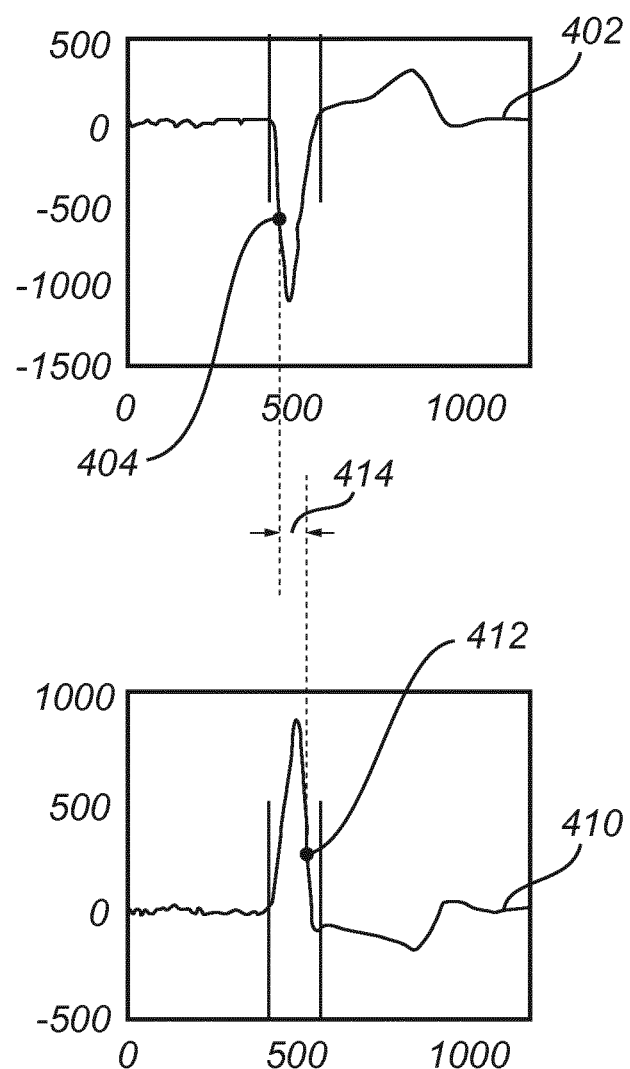
FIG. 4a shows a first and a second signal of an ECG for illustrating analysis of the ECG.

In FIG. 4a, the electrical signals of two leads, V1 and V5 are shown for illustrative purposes, showing a first signal 402 and a second signal 410. In FIG. 4a, a common time range of interest is indicated by two vertical lines.

The first signal 402 may be among the plurality of signals 202. A plurality of derivative values of the first signal 402 may be selected, step 306. The selection may be based on various criteria, such as a range of time instances, derivative values, sequential order, above or under a given threshold etc. In other words, the selection may be based on a range of time instances, derivative values, sequential order, above or under a given threshold, or a combination thereof.

A first point in time 404 of a first event may be determined based on the selected derivative values of the first signal 402. The selected derivative values may thus be analyzed according to predefined criteria in order to determine when the first event occurs, step 308. The first event may for example be an event of the heartbeat sequence in the first signal 402, such as a maximum negative derivative value of the first signal 402. Based on finding the first event, the first point in time 404 may thus be determined as the time instance in which the first event occurs. The first point in time 404 indicated in FIG. 4 corresponds to the maximum negative derivative value in the first signal 402.

The second signal 410 may be among the plurality of signals 202. A plurality of derivative values of the second signal 410 may further be selected, step 310.

The selection may be based on various criteria, such as a range of time instances, derivative values, sequential order, above or under a given threshold etc. The selection may be based on same or other criteria as the selection made for the derivative values of the first signal.

A second point in time 412 of a second event may be determined based on the selected derivative values of the second signal 410. The selected derivative values may thus be analyzed according to predefined criteria in order to determine when the second event occurs, step 312. The selected derivative values of the second signal may analyzed according to the same predefined criteria as the analysis performed for the first signal such that a second event corresponding to the first event is identified. The second event 412 may thus correspond to the first event and may for example be an event of the heartbeat sequence in the second signal 410, such as a maximum negative derivative value of the second signal 410. Based on finding the second event, the second point in time 412 may thus be determined as the time instance in which the second event occurs. The second point in time 412 indicated in FIG. 4a corresponds to the maximum negative derivative value in the second signal 410.

In an embodiment, the plurality of time instances may be within a QRS complex of a signal. Thus, derivative values may be calculated at a plurality of time instances within the QRS complex. Then, all or some of the calculated derivative values may be selected for further analysis.

According to another embodiment, the derivative values are continuously calculated at periodic time instances for an entire received signal. Then, the derivative values corresponding to time instances within the QRS complex of the signal may be selected.

The plurality of time instances may be specified before, during or after the analysis. For example, if a dyssynchrony is noticed, higher resolution might be needed and may therefore be changed during the process such that a shorter interval between sequential time instances is used.

A measure may be calculated, step 314, the measure being based on a difference 414 of the first point in time 404 and the second point in time 412. The measure may e.g. be a time delay between the first point in time 404 and the second point in time 412. The calculated measure may be an indication of a condition of the heart and may be of intermediate diagnostic relevance. For instance, the calculated measure may be an indication of dyssynchrony. Further description of different kinds of calculated measures will be given below.

Figure 4B:
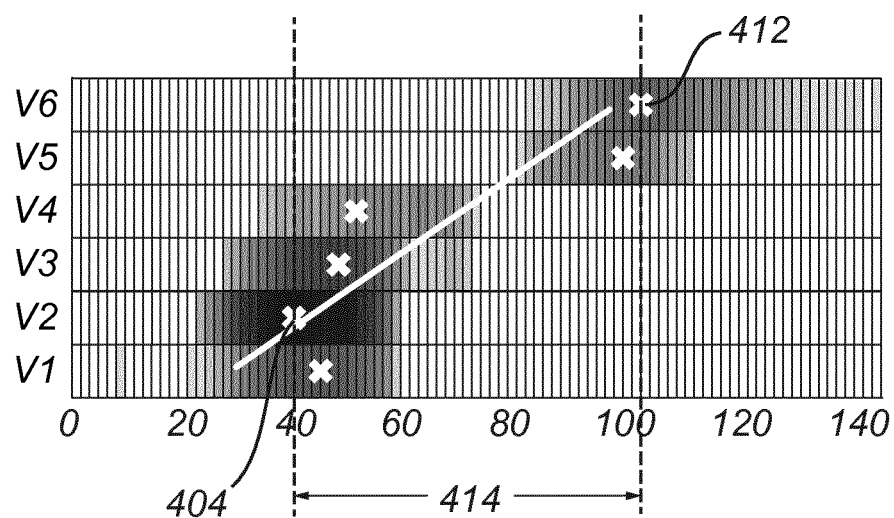
FIG. 4b shows a plot diagram of calculated derivative values for illustrating analysis of the ECG.

As shown in FIG. 4b and also further described below, the derivative values may be visualized by presenting a color plot (here illustrated in grayscale, where light areas represent positive or small, negative values and dark values represent large negative values) representing the derivative values stacked on top of each other in a common time range. An automatic determination of points in time 404 and 412 in the signals may thus be presented on a display, and an indication of the difference 414 of the first point in time 404 and the second point in time 412 may be shown. Alternatively, a physician or operator may indicate the first and second points in time in the presented color plot by interacting with the displayed color plot. Further, a physician may update or move points in time that have been automatically determined. Based on such manual selection, the measure 414 may then be calculated or an update of the measure 414 may be calculated.

Although the analysis of the acquired electrical signals is mainly described above as being performed in digital domain, it should be realized that the method may also be performed in analog domain.

As described above, a quantification of a condition of a heart may be determined by calculating of a measure. The calculated derivative values may also or alternatively be processed in order to facilitate visualization of the signals in order to simplify analysis of the condition of the heart to be made by a physician or operator.

Thus, the selected calculated derivative values in steps 306 and 310 may be compared to at least one threshold value. The comparison of the selected derivative values to at least one threshold value allows assigning the calculated derivative values to discrete ranges of values. Each range of values may be associated with a predefined visualization feature such that presentation of the derivative values may be facilitated.

If a single threshold value is used, such as zero, the visualization features may allow distinguishing between negative and positive derivative values. If several threshold values are used, distinguishing between several ranges of values is allowed.

The calculated derivative values may be selected in a common time range for the first and the second signals. Thus, for each time instance within the common time range, a corresponding derivative value for both the first signal and the second signal has been calculated.

The selected derivative values of the first and the second signals may thus be presented on a display, wherein the visualization features corresponding to the calculated derivative values for the first signal at a given time instance is presented below the visualization features corresponding to the calculated derivative values for the second signal at the given time instance. Thus, the visualization features for a plurality of time instances may be presented on a common time axis allowing a physician to immediately compare the two signals to each other.

The calculated measure may be presented together with the visualization features of the signals such that a physician may be able to compare a manual interpretation of the signals, based on the visualization of the calculated derivative values to a quantification of a condition of the heart. Further, the signals acquired by the respective leads may also be presented on a display allowing further manual analysis of the actually acquired signals.

Figure 5:
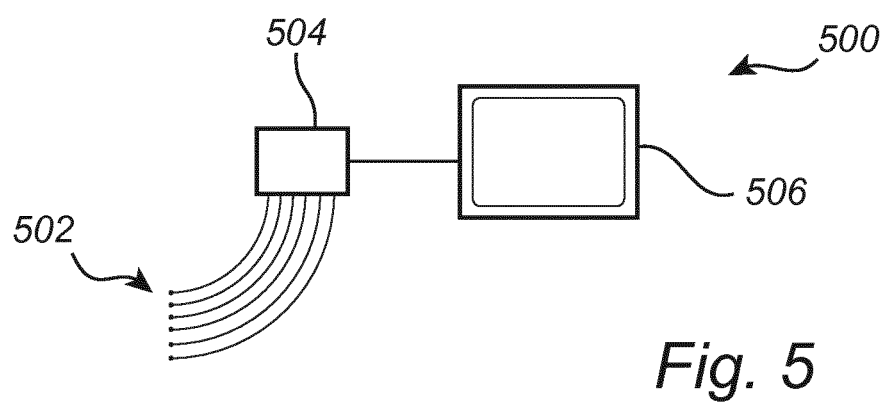
FIG. 5 is a schematic view of a device according to an embodiment.

Referring now to FIG. 5, a device 500 for analyzing a condition of a heart is described. The device 500 may comprise a plurality of leads 502 being configured to be arranged on the skin of a person or animal for acquiring a plurality of electrical signals of an ECG.

The leads 502 may be connected to a processing unit 504, which may thus be arranged to receive the electrical signals. The electrical signals may or may not be pre-processed, e.g. for smoothing and analog-to-digital conversion of the signals, before being received by the processing unit 504.

The processing unit 504 may be arranged as an application-specific integrated circuit (ASIC) arranged to execute a set of instructions. Alternatively, the processing unit 504 may be a general purpose microprocessor, such as a central processing unit (CPU), which may be provided with specific computer instructions so as to perform desired processing operations. The processing unit 504 may be arranged to perform the processing of the received signals as described above with reference to FIGS. 3 and 4. A computer program product may be provided for causing the processing unit 504 to perform the processing.

The processing unit 504 may be arranged in a type of computing device, portable or stationary, such as a laptop or a personal computer. The computing device may be provided with ports for connecting the leads 502 to the processing unit 504.

The processing unit 504 may further be connected to a display 506, e.g. via a port in the computing device or in a bus for connecting the processing unit 506 to a screen integrated in the computing device. Thus, the processing unit 504 may be arranged to output signals for causing presentation of the processed electrical signals on the display 506.

Figure 6:
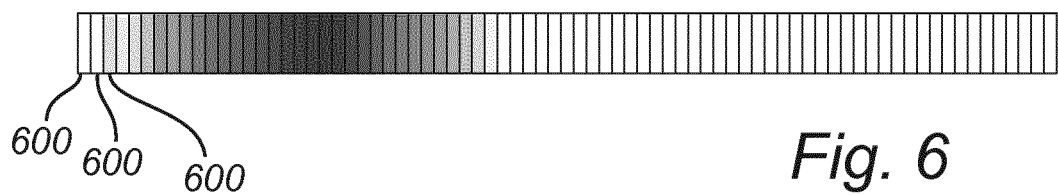
FIG. 6 illustrates a plot diagram of calculated derivatives of a single lead of an ECG at a plurality of time instances according to an embodiment.

Reference is now made to FIG. 6, in which a plot diagram of calculated derivative values is shown. The derivative values have been selected for a plurality of time instances 600. The derivative values may be represented by divergent color mapping, illustrated herein as a grayscale where light areas represent positive or small, negative values and dark values represent large negative values, of the derivative values. Each derivative value has been assigned a color corresponding to its numerical value. Other representations of the derivative values may be used, such as arrows, numbers or letters. A non-limiting example of representation is to let a '+' sign represent positive derivative values and a '−' sign represent negative values.

The negative derivative values represent a declining electrical activity, i.e. a lowering of the depolarizing wavefront. This can be caused by the wavefront reaching the epicardial wall of the heart. The plot diagram in FIG. 6 therefore shows, over time, the electrical propagation of the signal that controls the contraction of the heart at a spatially discrete region.

As discussed above, the signals may be constituted by the 12 leads used for acquiring of a standard 12-lead ECG. The signals may also be divided into subgroups such as leads aVL to III shown in FIG. 7a and leads V1-6 shown in FIG. 7b. The signals may further be divided into subgroups such as V1-3 and V4-6, representing different regions of the heart.

Figure 7A:
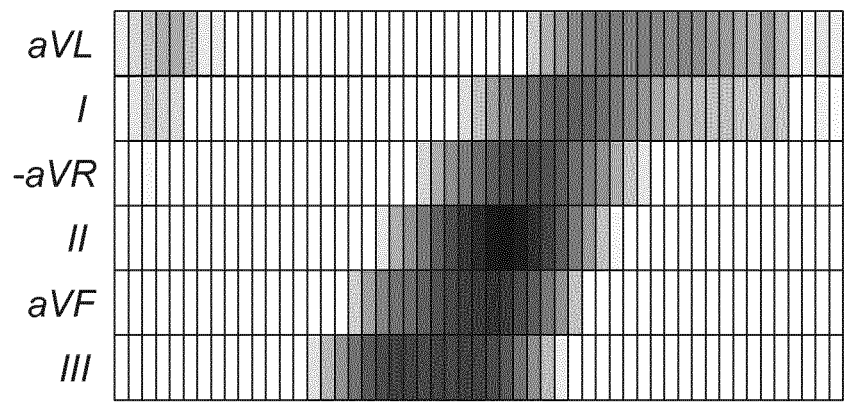
FIG. 7a illustrates a plot diagram of calculated derivatives of leads aVL, I, -aVR, II, aVF and III of an ECG according to an embodiment, displaying a healthy heartbeat.
Figure 7B:
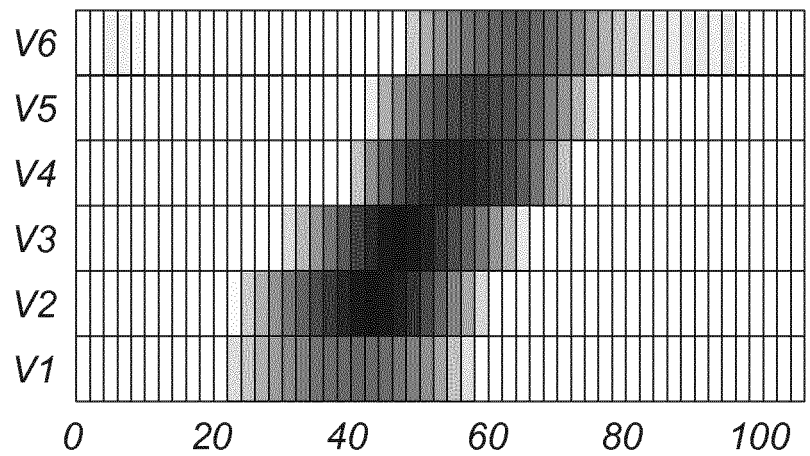
FIG. 7b illustrates a plot diagram of calculated derivatives of leads V1-6 of an ECG according to an embodiment, displaying a healthy heartbeat.

In FIGS. 7a-b the derivative values are represented by color mapping. As can be seen in the figure, a time shift between events in the signals is occurring. For example, the depolarization of lead V1 occurs earlier than that of V6. This is natural and occurs due to, among other things, difference in muscular wall thickness between the right and left ventricle. Although not illustrated, it is also possible to perform a similar observation for e.g. the right and left atria by selecting a plurality of time instances belonging to the P-wave of the ECG. Similarly, a plurality of time instances belonging to the ST segment or T-wave may be selected.

Figure 8:
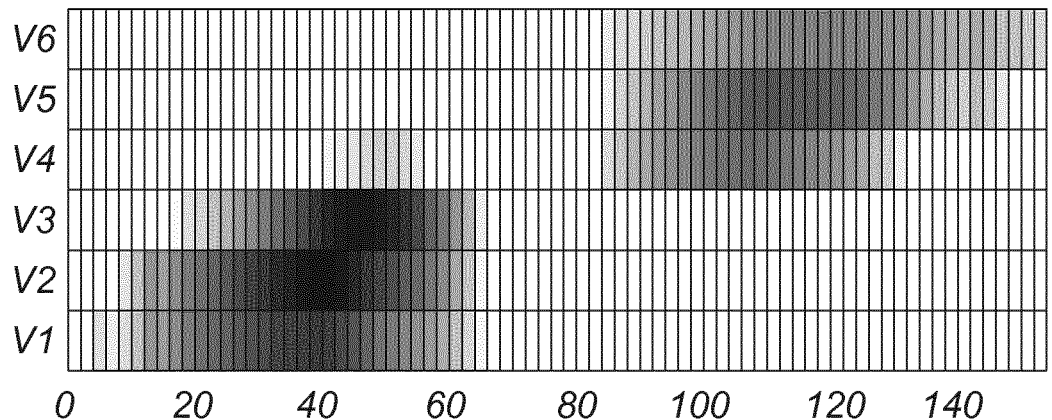
FIG. 8 illustrates a plot diagram of calculated derivatives of leads V1-6 of an ECG according to an embodiment, displaying a heartbeat suffering from dyssynchrony.

Referring to FIG. 8, derivative values of leads V1-6 are presented stacked on top of each other and color mapped. A shift between the subgroups V1-3 and V4-6 can be observed. The depolarization of the leads V4-6 is delayed and a sign of dyssynchrony. This may be immediately seen by the colors representing negative derivative values in the signals of leads V4-V6 being clearly shifted in the stacked presentation from the colors representing negative derivative values in the signals of leads V1-V3.

Thus, a presentation of the selected derivative values as illustrated in FIG. 8 may allow a physician to easily draw conclusions on the condition of the heart, such as determining dyssynchrony.

The presentation of the selected derivative values may be performed in real-time and may be updated for each heartbeat. Thus, the physician may continuously follow an illustration of the dyssynchrony from heartbeat to heartbeat. This may be particularly useful as a tool for aiding implantation of a pacemaker and configuring stimuli settings for the pacemaker. Thus, as pacemaker leads are arranged on the heart, the immediate result of the resynchronization provided by the pacemaker may be viewed on the display. The pacemaker leads may thus be optimally placed with use of the visualization and quantification of dyssynchrony provided by the device 500. Likewise, the stimuli settings for the pacemaker may be optimally configured.

A measure may be calculated based on the first point in the time 404 and the second point in time 412. The measure may for example be a time difference between the two points. The time difference may further be a measure between the depolarization events of different regions of the heart.

The measure may further be used as a sign of dyssynchrony of a heart. For example, the measure may be compared to a predefined optimal value. A measure that deviates from the optimal value may be a sign of dyssynchrony.

The number of events may be more than two, such as three or four events or even one or more events in each of six signals.

Figure 9:
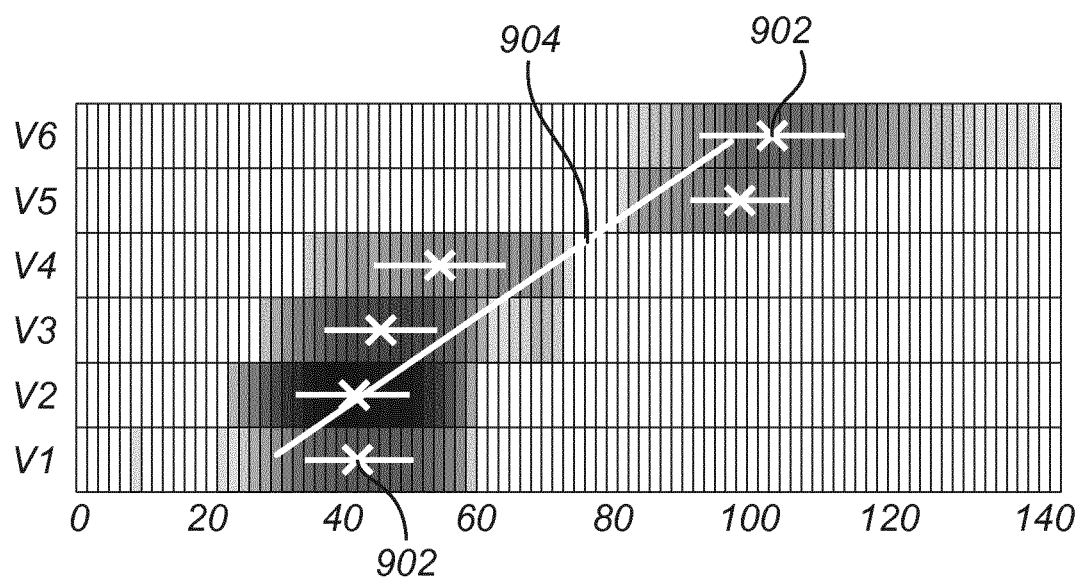
FIG. 9 illustrates a plot diagram illustrating calculation of a measure according to an embodiment of the method.

The skilled person realizes that there are other ways to alleviate the calculation of the measure. Such a way is illustrated in FIG. 9. In this diagram, the calculated derivative value at a given time is regarded as a weighing of this time instance. By regarding the entire signal, or selected plurality of points of the signal, in this way, a weighted center point can be found. The weighted center point could thus be extracted as a first feature of the signal, which may be used in determining a point in time of an event. A measure of the duration, or width, of the segment containing the negative slopes, could be calculated and extracted as a second feature of the signal which may be used in determining a point in time of an event, again regarding the calculated derivative value as a weight of each time instance.

Thus, in FIG. 9 these measured features are shown atop a color mapping indicating the amplitude of negative derivative values at each time instance. Events may then be identified from these features, e.g. as a point in time of the weighted center point, as illustrated by crosses 902. A measure of the difference of points in time may then be calculated by comparing the points in times of the events.

Yet another method would be to make a diagram, where the calculated derivative values from a multitude of heartbeats from a single lead are analyzed. In such a diagram, the value at each time instance is the number of negative calculated derivative values occurring at the time instance over the multitude of heartbeats. Thus, a distribution of the negative derivative values within a heartbeat could also be illustrated as a color mapping similar to the diagram in FIGS. 7 to 9. Events may then be identified in the distribution of the derivative values for each signal, e.g. as a time instance where the maximum number of negative derivative values occurs. A measure may then be calculated by comparing the points of times of the events.

According to an embodiment, lines 904 can be fitted in order to analyze the distributed calculated derivative values. The coefficients of the fitted line may provide insight into a condition of dyssynchrony of the heart. For example, a linear relation between the distributions of negative calculated derivative values may provide evidence of a healthy heart, while a parabolic relation between the distributions may be a sign of dyssynchrony. Also, the coefficients of the fitted lines may be used as measures of dyssynchrony, such that a healthy heart should have a steep slope of a linear fitted line, whereas a heart with dyssynchrony may have a gentle slope. Also, the direction of the slope may be used as a measure of dyssynchrony for example to infer that the left ventricle is electrically delayed with respect to the right ventricle or vice versa. Also, coefficients of a second order polynomial fitted line may be used as measures of dyssynchrony.

The fitted lines may be formed by using maximum values, weighted mean values or distributions of derivative values. The fitted lines may be formed by using equal weighing of time instances. Further, any number of center points may be used to calculate a feature of the signal. Also, the duration of the distributions of negative calculated derivative values may be used to infer knowledge about propagation in a location of the heart.

Further, additional measures may also be formed which may facilitate determination of dyssynchrony, possibly in combination with measure(s) as described above.

For instance, the summation of negative derivative values across leads may also be used to infer knowledge about dyssynchrony between the ventricles in the heart. For example, by quantifying the number of peaks in the distribution of summed negative derivatives across leads, or by measuring the difference in time between different peaks, or as the difference in amplitude between such peaks.

The time instances of the beginnings and ends of the distributions of negative derivatives in each lead may also be used to infer knowledge about the dyssynchrony between the ventricles in the heart. For example, by measuring the difference in time between the beginning of a first distribution of negative derivatives and the beginning of a second distribution of negative derivatives or any combination of the beginning and end of a first distribution of negative derivates and the beginning or end of a second distribution of negative derivates including any combination of the beginning and end of a distribution of negative derivatives in groups of leads.

The magnitude of the negative derivatives or the duration of negative derivatives either in a single band or as a cluster of bands may also be used to infer knowledge about dyssynchrony between the ventricles in the heart.

Knowledge about dyssynchrony between the ventricles in the heart may also be obtained by expressing the difference in magnitudes of negative derivatives as a fraction of the time interval between the occurrences of the negative derivatives.

Knowledge about dyssynchrony between the ventricles in the heart may also be obtained by expressing dyssynchrony measurements as a fraction of QRS complex duration.

Additionally, knowledge about dyssynchrony between the ventricles in the heart may also be inferred by changes in dyssynchrony measurements from a first ECG to a second ECG recording.

The person skilled in the art realizes that the present invention by no means is limited to the preferred embodiments described above. On the contrary, many modifications and variations are possible within the scope of the appended claims.

For example, the measure may be represented in many other forms, such as percentage of synchronization or healthy/non-healthy condition.

Additionally, variations to the disclosed embodiments can be understood and effected by the skilled person in practicing the claimed invention, from a study of the drawings, the disclosure, and the appended claims.

The invention claimed is:

1. A method of selecting patients with cardiac dyssynchrony, comprising
placing electrodes at specific positions on the torso,
receiving a plurality of electrical signals, which are acquired by non-invasive measurement on the skin of a patient with said electrodes, each signal representing electrical activity in a respective region of the heart of the patient, wherein the electrical activity contributes to controlling mechanical activation of the heart,
calculating a derivative value of each signal at a plurality of time instances, wherein the plurality of time instances is within a time domain of a heartbeat of the heart,
selecting a plurality of the calculated derivative values of a first signal among the plurality of signals and determining at least a first point in time of a first event based on the selected derivative values of the first signal,
selecting a plurality of the calculated derivative values of a second signal among the plurality of signals and determining at least a second point in time of a second event, corresponding to the first event, based on the selected derivative values of the second signal,
wherein the derivative value is calculated as a slope at a point of a continuous curve of the first or second signal;
calculating at least one measure based on a difference of the at least first point in time and the at least second point in time, by
calculating a time difference between the at least first point in time and the at least second point in time, and
calculating at least one measure based on said time difference, and
using the calculated at least one measure to select patients with cardiac dyssynchrony.

2. The method according to claim 1, wherein the plurality of time instances is within a QRS complex.

3. The method according to claim 2, wherein the plurality of time instances is within a single QRS complex.

4. The method according to claim 1, wherein the plurality of time instances is within a P-wave, a T-wave, or a ST-segment.

5. The method according to claim 4, wherein the selected derivative values of the first signal and the selected derivative values of the second signal have been calculated at the same time instances in a range of time instances from onset of a P-wave, T-wave, or ST-segment in the first signal to offset of the P-wave, T-wave, or ST-segment in the second signal.

6. The method according to claim 4, wherein the time instances of the selected derivative values of the first and second signal are from the same stage of the P-wave, T-wave, or ST-segment.

7. The method according to claim 1, wherein the derivative value is a first derivative value.

8. The method according to claim 1, wherein the selected derivative values of the first signal and the selected derivative values of the second signal have been calculated at the same time instances in a range of time instances from onset of a QRS complex in the first signal to offset of the QRS complex in the second signal.

9. The method according to claim 1, wherein the time instances of the selected derivative values of the first and second signal are from the same stage of the QRS complex.

10. The method according to claim 1, wherein the calculating of a measure further comprises comparing a mean value of the selected derivative values of the first signal to a mean value of the selected derivative values of the second signal.

11. The method according to claim 1, wherein the calculated measure is representative of a time shift between occurrence of a negative or positive slope of a QRS complex in the first signal and occurrence of a negative or positive slope of a QRS complex in the second signal.

12. The method according to claim 1, wherein the calculated measure is representative of a time shift between occurrence of a negative or positive slope of a P-wave, T-Wave, or ST-segment in the second signal.

13. A method of selecting patients with cardiac dyssynchrony, comprising
placing electrodes at specific positions on the torso,
receiving a plurality of electrical signals, which are acquired by non-invasive measurement on the skin of a patient with said electrodes, each signal representing electrical activity in a respective region of the heart of the patient, wherein the electrical activity contributes to controlling mechanical activation of the heart,
calculating a derivative value of each signal at a plurality of time instances, wherein the plurality of time instances is within a time domain of a heartbeat of the heart extending at least from onset of a QRS complex in a first signal to offset of the QRS complex in a second signal, and wherein the derivative value is calculated as a slope at a point of a continuous curve of the first or second signal,
selecting a plurality of the calculated derivative values of the first signal among the plurality of signals and determining at least a first point in time of a first event based on the selected derivative values of the first signal,
selecting a plurality of the calculated derivative values of the second signal among the plurality of signals and determining at least a second point in time of a second event, corresponding to the first event, based on the selected derivative values of the second signal, comparing each of the selected derivative values of the first signal and each of the selected derivative values of the second signal to at least one threshold value, calculating a time difference between the at least first point in time and the at least second point in time, calculating at least one measure based on said time difference, and using the calculated at least one measure to select patients with cardiac dyssynchrony.

14. The method according to claim 13, wherein the selected derivative values are assigned a first state if the selected derivative value is positive and a second state if the selected derivative value is negative.

15. The method according to claim 13, wherein the selected derivative values are compared to a color scale for assigning a color to each selected derivative value.

16. The method according to claim 13, further comprising outputting color information based on the assigned colors to a display for presenting a color-coding of the selected derivative values on the display.

17. A computer program product comprising a computer-readable medium with computer-readable instructions such that when executed on a processing unit the computer program will cause the processing unit to perform a method according to claim 13.

18. A device for selecting patients with cardiac dyssynchrony, comprising a processing unit, wherein the processing unit is configured to:

receive a plurality of electrical signals, which are acquired by non-invasive measurement on the skin of a patient with electrodes placed at specific positions on the torso, each signal representing electrical activity in a respective region of the heart of the patient, wherein the electrical activity contributes to controlling mechanical activation of the heart, wherein the processing unit is further configured to:

calculate a derivative value of each signal at a plurality of time instances, wherein the plurality of time instances is within a time domain of a heartbeat of the heart, select a plurality of the calculated derivative values of a first signal among the plurality of signals and determine at least a first point in time of a first event based on the selected derivative values of the first signal, select a plurality of the calculated derivative values of a second signal among the plurality of signals, and determine at least a second point in time of a second event, corresponding to the first event, based on the selected derivative values of the second signal, wherein the derivative value is calculated as a slope at a point of a continuous curve of the first or second signal;

calculate a time difference between the at least first point in time and the at least second point in time, calculate at least one measure based on said time difference, and use the calculated at least one measure to select patients with cardiac dyssynchrony.

19. The device according to claim 18, further comprising electrocardiogram leads for acquiring said plurality of electrical signals.

20. A computer program product comprising a computer-readable medium with computer-readable instructions such that when executed on a processing unit the computer program will cause the processing unit to perform a method according to claim 1.

* * * * *